US009848910B2

(12) United States Patent
MacLean (10) Patent No.: US 9,848,910 B2
(45) Date of Patent: Dec. 26, 2017

(54) MEDICAL DEVICE FOR TISSUE ABLATION AND RELATED METHODS OF USE

(71) Applicant: BOSTON SCIENTIFIC SCIMED, INC., Maple Grove, MN (US)

(72) Inventor: Brian MacLean, Acton, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1030 days.

(21) Appl. No.: 13/777,117

(22) Filed: Feb. 26, 2013

(65) Prior Publication Data

US 2013/0226195 A1    Aug. 29, 2013

Related U.S. Application Data

(60) Provisional application No. 61/604,283, filed on Feb. 28, 2012.

(51) Int. Cl.
*A61B 17/42* (2006.01)
*A61M 29/00* (2006.01)
*A61B 18/04* (2006.01)
*A61B 18/00* (2006.01)

(52) U.S. Cl.
CPC .............. *A61B 17/42* (2013.01); *A61B 18/04* (2013.01); *A61M 29/00* (2013.01); *A61B 2018/00279* (2013.01); *A61B 2018/00559* (2013.01); *A61B 2018/00577* (2013.01); *A61B 2018/00642* (2013.01); *A61B 2018/00791* (2013.01); *A61B 2018/00875* (2013.01); *A61B 2018/00982* (2013.01); *A61B 2018/046* (2013.01)

(58) Field of Classification Search
CPC .................. A61B 18/04; A61B 18/082; A61B 2018/00559; A61B 2018/00577; A61B 2018/044; A61B 2018/046; A61B 17/42; A61B 2017/4216; A61B 2017/4233
See application file for complete search history.

(56) References Cited

U.S. PATENT DOCUMENTS

| | | | | |
|---|---|---|---|---|
| 5,542,928 A | * | 8/1996 | Evans et al. | 604/113 |
| 6,009,877 A | * | 1/2000 | Edwards | A61B 5/04884 |
| | | | | 128/898 |
| 6,187,346 B1 | * | 2/2001 | Neuwirth | 424/618 |
| 6,960,203 B2 | * | 11/2005 | Xiao et al. | 606/27 |

* cited by examiner

*Primary Examiner* — Todd J Scherbel
(74) *Attorney, Agent, or Firm* — Fay Kaplun & Marcin, LLP (57) ABSTRACT

A medical device for ablating tissue within a body cavity includes a sheath having a lumen extending therethrough from a proximal end to a distal end and a first channel extending within the lumen, an end-effector extending from a proximal end to a distal end and including an expandable member having a plurality of arms extending between the proximal end and the distal end. The arms are configured to transition between a collapsed state and an expanded state and a mechanism for transporting a fluid through one of the channels to the body cavity to ablate the tissue.

11 Claims, 5 Drawing Sheets

MEDICAL DEVICE FOR TISSUE ABLATION AND RELATED METHODS OF USE

PRIORITY CLAIM

The present application claims priority benefit to U.S. Prov. Patent Application Ser. No. 61/604,283 filed Feb. 28, 2012, the specification of which is incorporated herewith by reference.

FIELD OF THE INVENTION

Embodiments of the present disclosure relate generally to medical devices suitable for use in medical procedures. In particular, embodiments of the instant disclosure relate to medical devices and methods that include body tissue manipulation.

BACKGROUND OF THE INVENTION

Tissue ablation is employed in the treatment of various ailments. One such situations where it may be desirable to perform a tissue ablation is for the treatment of a condition in the female reproductive system called menorrhagia, which causes excessive or prolonged uterine bleeding during a menstrual cycle.

One treatment procedure for menorrhagia is called endometrial ablation, which involves the treatment of selected portions of tissue with a heated fluid, referred to as hydrothermal ablation. The hydrothermal procedure involves flushing a high-pressure heated fluid within the uterine cavity for a specific time period to ablate the tissue.

Hydrothermal procedures use free flowing boiling water or saline to destroy the endometrial lining. High-pressure fluid can flow to each and every section of the cavity, and is not limited by irregularities or small sub mucosal fibroids within the cavity. The potential downside of using a high-pressure fluid is that the fluid can leak into undesirable areas such as fallopian tubes and possibly cause inadvertent burns.

The fallopian tubes are generally under slightly higher pressure than the uterus, but the high-pressure fluid used during hydrothermal ablation may be sufficient to force fluid into the fallopian tubes, which can result in undesired tissue burning. One technique to avoid damaging undesired tissue is to reduce the pressure of the fluid. At a reduced fluid pressure, however, the uterus may remain collapsed, and the resulting tissue-to-tissue contact may prevent efficient ablation.

Therefore, there exists a need for an improved hydrothermal tissue ablation device and method that allows usage of low-pressure fluid to reduce the likelihood of tissue damage.

SUMMARY OF THE INVENTION

Embodiments of the present disclosure direct towards systems and methods for tissue ablation within a body cavity.

One embodiment of the present disclosure is directed towards an exemplary medical device for ablating tissue within a body cavity using a fluid. The medical device includes a sheath having a proximal end, a distal end, and a lumen extending between the proximal and distal ends. One or more working channels extend within the lumen of the sheath. An end effector, disposed at the distal end of the sheath, includes a proximal end, a distal end, and an expandable member having arms extending between its proximal end and the distal end. The arms are configured to transition between a collapsed state and an expanded state. The medical device further includes a mechanism for transporting fluid through one of the channels to the body cavity to ablate the tissue.

An exemplary method according to another embodiment of the invention is directed toward ablating tissue within a body cavity. The method includes introducing a medical device into the body cavity. The medical device includes an end-effector having an expandable member and a mechanism for transporting a fluid to the body cavity to ablate the tissue. The method further includes expanding the expandable member provided on the end-effector to expand the body cavity. The method also includes ablating a lining of the body cavity by providing a fluid through the mechanism.

It is to be understood that both the foregoing general description and the following detailed description are exemplary and explanatory only and are not restrictive of the invention, as claimed.

DETAILED DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing the device in the patient.

The embodiments of the present disclosure are directed towards medical devices that enable effective body cavity tissue ablation. The medical device includes a sheath having a proximal end, a distal end, and a lumen extending between the proximal and distal ends. One or more working channels extend between the lumen of the sheath from proximal to distal end. For the ablation process, the present disclosure employs low-pressure heated fluid injected into a body cavity through one or more working channels of the lumen. A body cavity, such as uterus, is generally urged towards its collapsed state (e.g., by surrounding tissues), so expansion of the cavity may be required to expose all the surface area of tissues to be ablated. As low-pressure fluids may not adequately expand the cavity, embodiments of the present disclosure employ an end-effector disposed at the distal end of the sheath for this purpose. Further, the medical device may include any other devices typically used in tissue manipulation procedures, without departing from the present disclosure's scope.

The end-effector is configured as an expandable member with an elongate member attached to its proximal end. The expandable member may be a basket that moves between two configurations—expanded and collapsed. The expandable member remains collapsed within a working channel of the sheath during insertion and retrieval of the device. Once deployed to a desired position within a target body cavity, the expandable member is extended from the distal end of the sheath and expanded radially outward. The expanded state of the basket increases the body cavity size by pushing the surrounding tissue outwardly. This expansion of the cavity separates the opposing surfaces of the cavity to expose these surfaces to a low-pressure ablation fluid (i.e., fluid at a pressure less than a tissue pressure applied to the cavity by surrounding tissues) as will be described in more detail below.

The described embodiments of the present disclosure relate to tissue ablation or a tissue manipulation procedure. It will be understood by those in the art that the medical device may be employed for other medical procedures.

Figure 1:
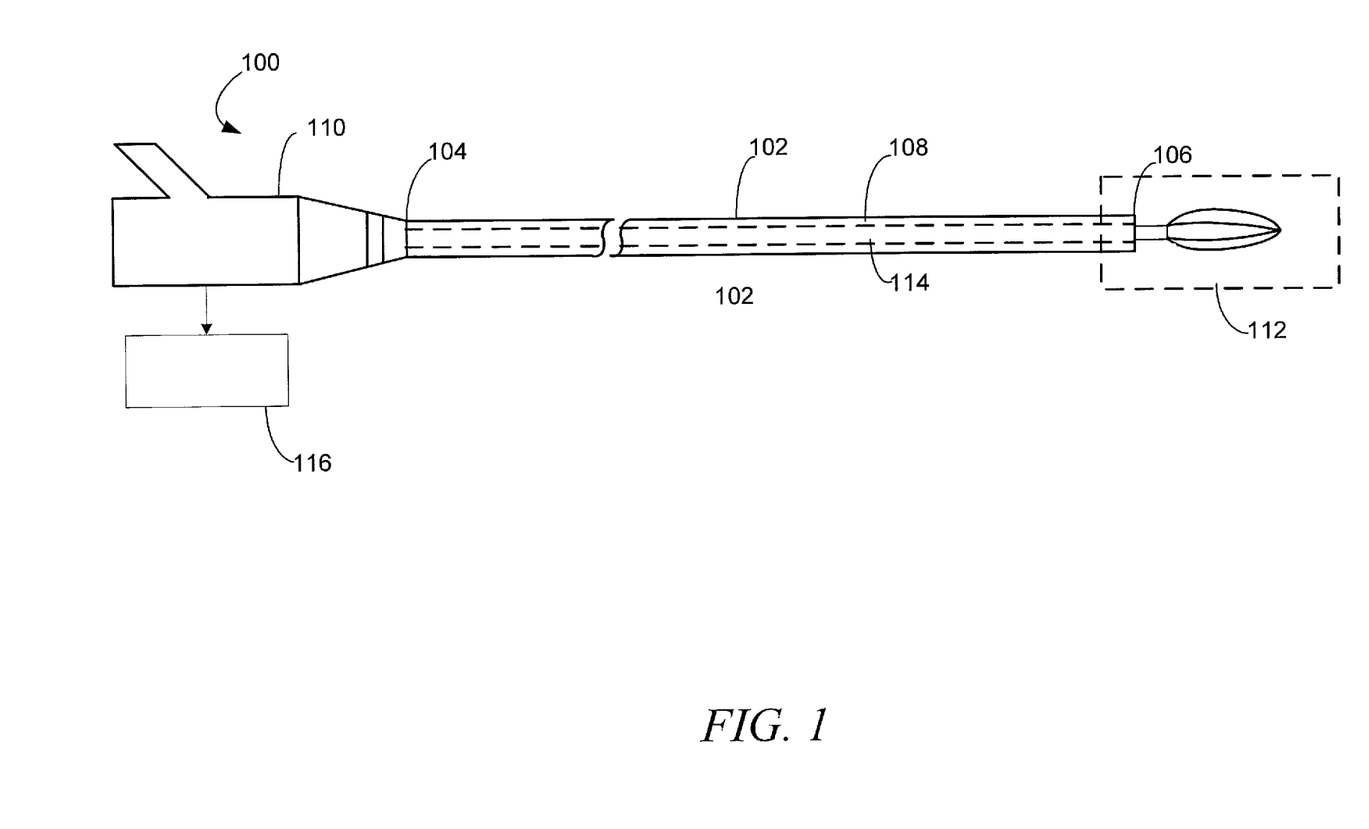
FIG. 1 is a schematic view of an exemplary medical device according to embodiments of the present disclosure.

FIG. 1 illustrates an exemplary medical ablation device 100 according to an embodiment of the present disclosure. The device 100 includes a sheath 102 having a proximal end 104, a distal end 106, and a lumen 108 extending between the proximal and distal ends 104, 106. The device 100 also includes one or more working channels 114 running within the lumen 108 of the sheath 102 from its proximal end 106 to its distal end 104. The ablation device 100 further includes a handle 110 coupled to the proximal end 104 of the sheath 102 and an end-effector 112 coupled to its distal end 106. The ablation device 100 may also include one or more ports on the sheath 102 or the handle 110 to connect external equipment to the working channels 114 of the sheath 102. The ablation device is also adapted to be connected to a fluid reservoir 116 that stores a fluid, which may be a low pressure saline.

The sheath 102 may be a substantially circular and it may be made of any suitable biocompatible material such as polyurethane, plastic, or any other such material. Other suitable cross-sectional shapes such as elliptical, oval, polygonal, or irregular may also be contemplated. Moreover, the sheath 102 may be rigid along its entire length, flexible along its entire length, or adapted for flexure along portions of its length. Alternatively, the sheath's distal end 106 may be flexible while the remaining sheath 102 may be rigid. Flexibility allows the sheath 102 to maneuver in the circuitous vasculature, while rigidity provides the required force to urge the sheath 102 forward.

The outer surface of the sheath 102 may include coatings. For example, sheath 102 may include a lubricious coating to facilitate convenient insertion through a body lumen or surgical insertion. Further, to detect the sheath's 102 position within a patient's body, at least some portions of the sheath 102 may include radiopaque materials such as gold, palladium, platinum, tantalum, tungsten alloy, or polymeric materials loaded with radiopaque agents such as barium sulfate ($BaSO_4$) or bismuth sub carbonate (($BiO)_2CO_3$). Radiopaque materials are capable of producing a relatively bright image on a fluoroscopic monitor or other imaging device.

The sheath 102 and the end-effector 112 may further be coated with an anti-bacterial covering to inhibit bacterial growth on their surfaces. The anti-biotic coating may contain an inorganic anti-biotic agent, disposed in a polymeric matrix that adheres to the antibiotic agent to the sheath 102 and end-effector 112 surfaces. Further, a drug-releasing coating may also be applied to their outer surface, assisting in delivery of drugs to the severing site.

Operators may insert multiple medical devices through the working channels 114 to perform various procedures simultaneously. For example, the operator may place tissue manipulation tools in one or more channels and a visual tool in another channel. For ablation purposes, one of the working channels 114 may allow fluid into and out of the distal end 106 of the sheath 102. It will be understood that other exemplary tools may also be inserted in the working channels 114 without departing from the scope of the present disclosure.

Further, the handle 110 may include one or more ports for inserting tools within the ablation device 100. The handle 110 may further include means to navigate the distal end 106 of the sheath 102 within a patient's body. Such means may include mechanical, electronic, or combination means. Further, the handle 110 may include control buttons to actuate the end-effector 112.

Figure 2:
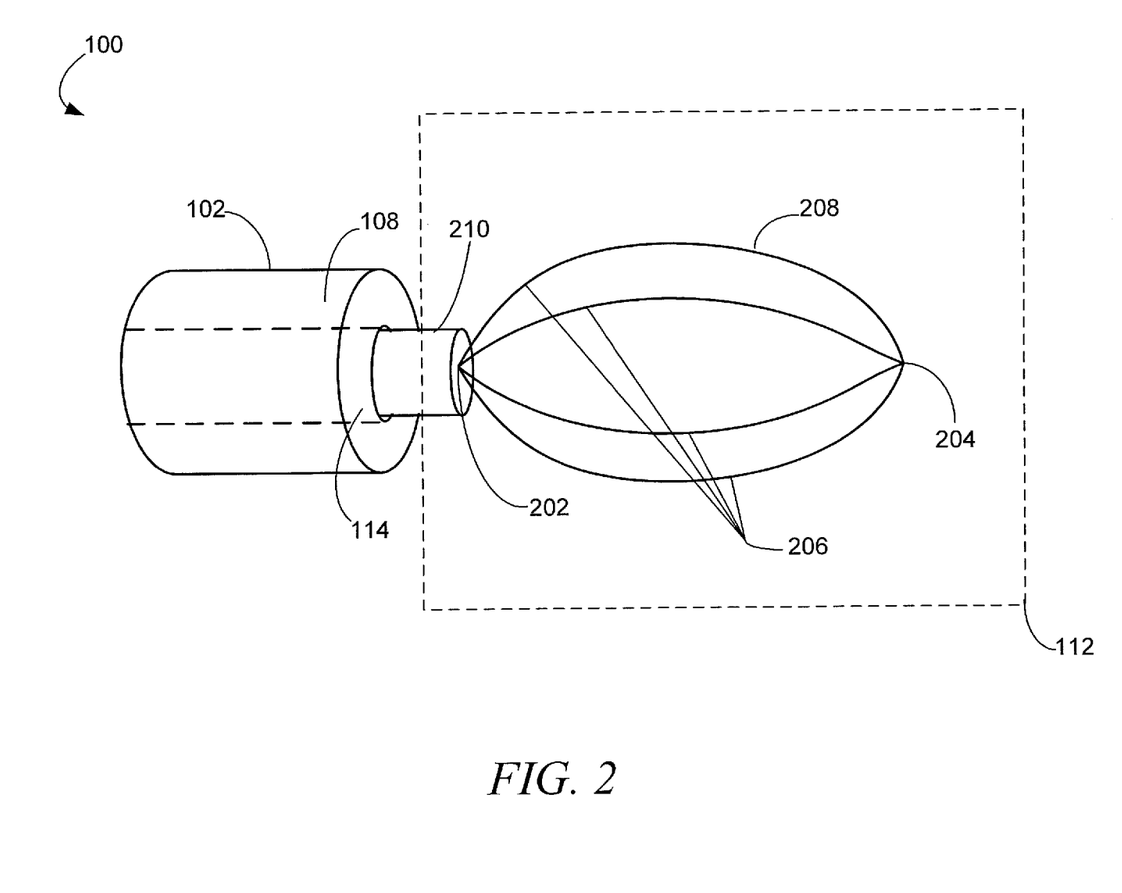
FIG. 2 illustrates the distal end of the medical device of FIG. 1.

FIG. 2 illustrates the distal end 106 of the ablation device 100 depicting the end-effector 112. As shown, the end-effector 112 includes an expandable member 208 and an elongate member 210 connected to the proximal end 104 of the expandable member 208. The elongate member 210 may be disposed within the working channel 114 of the lumen 108, while the expandable member 208 extends from the distal end 106 of the sheath 102. The expandable member 208 is configured to be movable between expanded and collapsed configurations.

The elongate member 210 may be formed of one or more flexible or rigid members (e.g., a wire, a group of wires, a tube connected to the proximal end 202 of the expandable member 208, etc.). The elongate member 210 may be made up of a metal or a polymeric substance, or a combination of the two.

The elongate member 210 may extend within the working channel 114 from the proximal end 104 of the sheath 102 to the distal end 106 and may be used to control the movement of the expandable member 208 within the working channel 114. The elongate member 210 may also hold a mechanism (not shown) to control the expansion and contraction of the expandable member 208. The mechanism may be mechanical, electronic or a combination thereof. In one embodiment, expansion and contraction of the expandable member 208 is affected by either extending or withdrawing the basket 208 from within the working channel 114, as explained below.

In the illustrated embodiment, the expandable member 208 is configured as a basket 208 having a proximal end 202, a distal end 204, and multiple arms 206 extending between the proximal and distal ends 202, 204. Arms 206 are joined together along the longitudinal axis at the proximal and distal ends 202, 204 of the expandable member 208. In a preferred embodiment, the expandable member comprises three to four arms 206 although any other number of arms 206 may be used without deviating from the scope of the invention.

In the illustrated embodiment, arms 206 extend axially from the proximal end 202 to the distal end 204 of the expandable member 208. In other embodiments, however, arms 206 may follow a spiral or helical path from the proximal end 202 to the distal end 204. It will be understood that other configurations of the expandable member 208 are also within the scope of the present disclosure. In all embodiments, however, arms 206 remain substantially parallel to the longitudinal axis in the collapsed state, and radially expand in the expanded state.

Each arm 206 may be formed of a single wire extending from the proximal end 202 to the distal end 204. Alternatively, each arm 206 may be formed of multiple wires extending along the entire length of the expandable member 208. In some implementations, the thickness of the wires may be uniform along the length of the arms 206. Alternatively, the wires may be thicker in the center and thinner at the proximal and distal portions of the arms 206, or vice-versa.

The arms 206 may include suitable coatings, such as antibacterial coatings, lubricious materials, drug-releasing agents, or radiopaque markers. It will be understood that these or any other known medical device coating may be applied to the arms 206 without departing from the scope of the present disclosure.

Figure 3A:
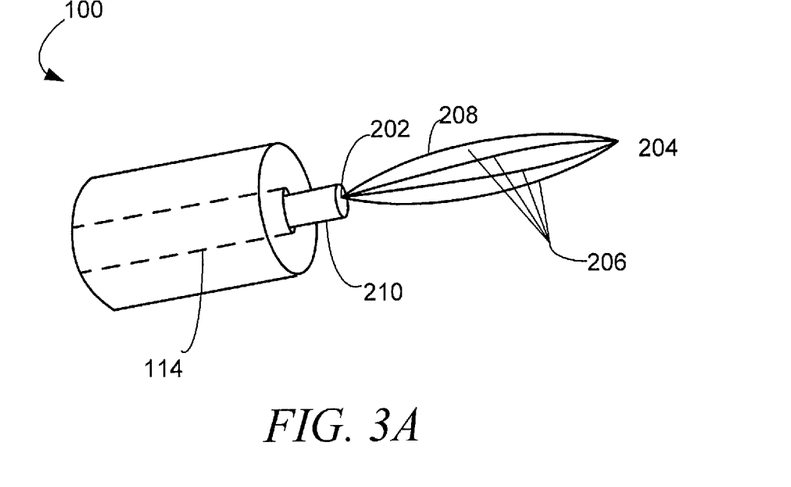
FIG. 3A depicts the end-effector of the medical device, shown in FIG. 1, in an expanded state.
Figure 3B:
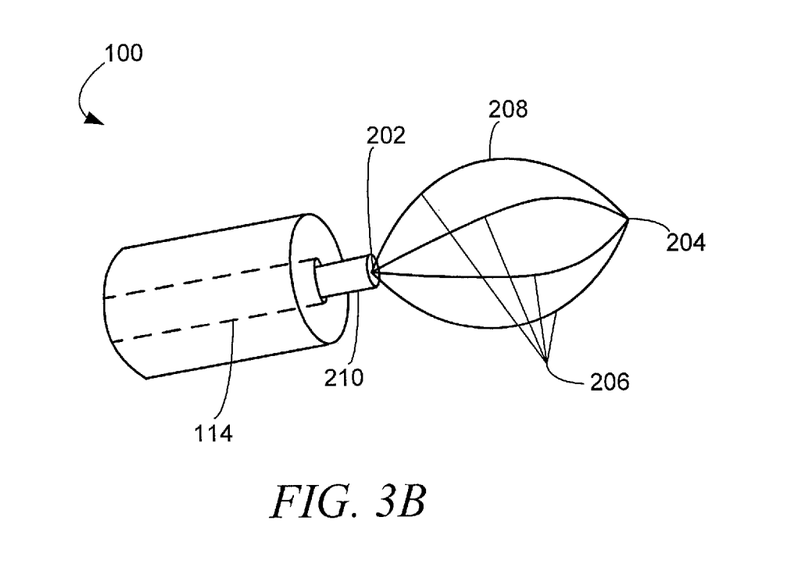
FIG. 3B depicts the end-effector of the medical device, shown in FIG. 1, in a collapsed state.

FIGS. 3A & 3B are perspective views of the end-effector 112 in the collapsed and expanded configurations, respectively. In the collapsed configuration, the expandable member 208 may lie within the working channel 114 of the sheath 102, a diameter of the expandable member 208 being sufficiently small to permit slidable insertion into the working channel 114. Once the sheath 102 is deployed, the expandable member 208 may extend distally out of the distal end 106 of the sheath 102 and expand in a radial direction. In the expanded state, the diameter of the basket 208 may be sufficiently large to support the body cavity tissue from collapsing.

To shift between the collapsed and expanded states, the expandable member 208 may be self-expandable, or expanded by some external force. To return the self-expandable expandable member 208 into a collapsed state, however, an external force may be required. Many techniques may be utilized to apply force on a self-expandable expandable member 208 and keep it in the collapsed state. Suitable materials to form the self-expandable expandable member 208 may include shape memory alloys, such as nitinol, stainless steel, etc. It will be understood that any other material now known or known in the future may just as easily be used to form the self-expandable expandable member 208.

According to one technique, the self-expandable expandable member 208 may be present within sheath 102 for deployment. Sheath 102 exerts a radially inward pressure on the self-expandable expandable member 208, keeping it in the collapsed state. Once the expandable member 208 exits sheath 102, however, the pressure is released, and the self-expandable expandable member 208 expands. It will be understood that in such situations, the material and thickness of sheath 102 is selected such that it applies a greater force on the self-expandable expandable member 208 than the force exerted by the expandable member 208 on sheath 102. If the sheath 102 material is too thin or too elastic, it may not be sufficient to hold the self-expandable expandable member 208 in the collapsed state and the member may expand within the sheath 102 itself. Alternatively, if sheath 102 is too rigid or thick, it may not be able to traverse the circuitous path within a patient's body, causing injury. Therefore, it may be often preferred to select a suitable material and thickness keeping both aspects in mind.

According to another technique, pull wires (not shown) may be utilized. Pull wires may be attached to one of the distal end 106 or proximal end 104 of the expandable member 208. When the pull wire is pulled in a certain axial direction (distally or proximally), it places a tensile force on the expandable member 208, stretching it longitudinally and compressing it radially. When the pull wire is released, the tensile force is released permitting the expandable member 208 to expand. For example, if the pull wire is attached to the distal end 106, pulling the wire distally elongates (compresses) the member and releasing the pull wire releases the force on the expandable member 208, expanding it. Moreover, a mechanism to pull, push, or release the pull wire may be provided in the handle 110 allowing operators to easily expand or compress the member, as required. Alternatively, the actuation mechanism may be present external to handle 110.

Alternatively, expandable member 208 may require an external force for expansion. In some cases, the expandable member 208 may remain in the expanded state as long as the external force exists and return to the collapsed state once the force ceases to exist. Other embodiments of the expandable member 208 may be able to maintain the expanded state even after the external force ceases to exist. An opposite force may then be required in such embodiments of the expandable member 208 to bring them back into the collapsed state. Many such means may be utilized without departing from the scope of the present disclosure. For example, means such as springs or levers may be utilized to expand the expandable member 208. Similarly, the expandable member 208 may be configured to include pivotal structures connected to one another. For instance, the expandable member 208 may be formed of multiple wires connected to one another along pivotal joints (not shown). An outward force on the pivotal joints expands the various wires connected to the joint, expanding the expandable member 208.

The expansion of the expandable member 208 should be such that it does not cause damage to the cavity. For example, excessive expansion or expansion force may damage internal cavities. To prevent such large expansion diameters, the member may include visualization aids, such as cameras or fluorescent dyes, to visualize the extent of expansion.

Figure 4:
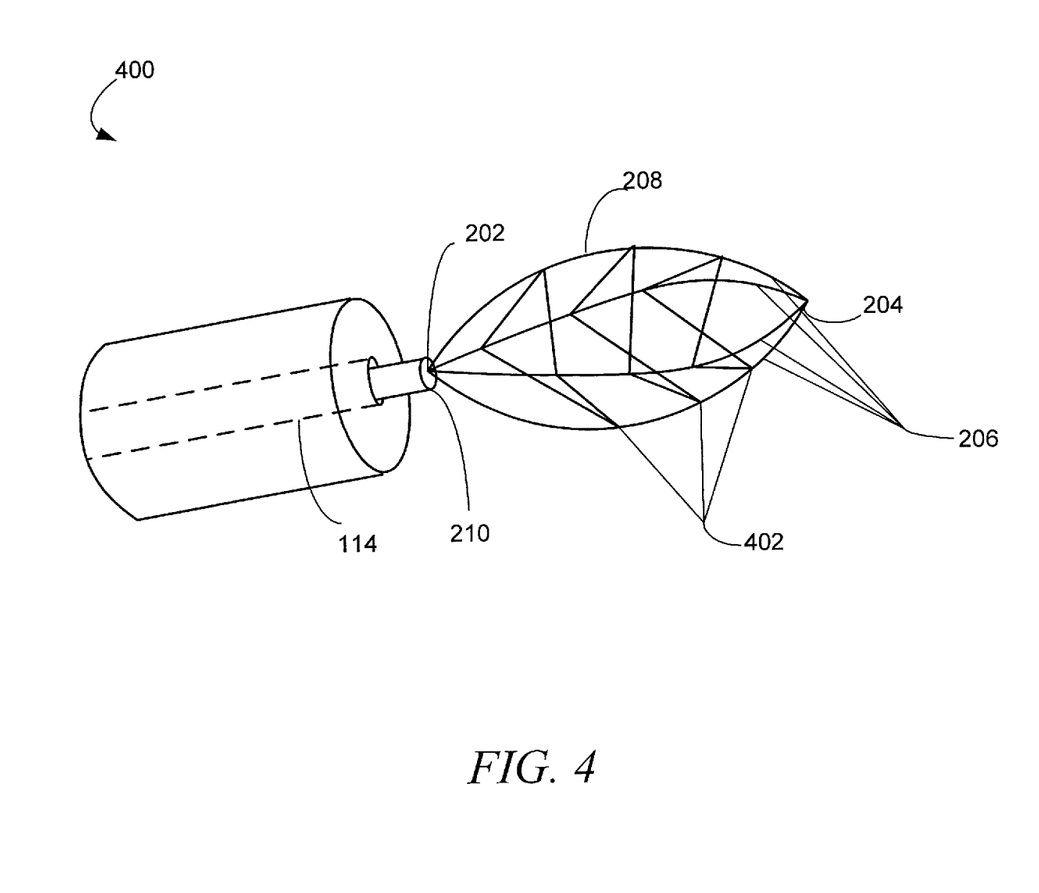
FIG. 4 is an alternate embodiment of the end-effector, shown in FIG. 2.

Further, the expandable member 208 may include a force or expansion-limiting component that prevents the expandable member 208 from expanding beyond a certain limit. Often, the expansion limit may be set during manufacture. For example, operators may know the average body cavity sizes, and they may ensure that the expandable member 208 does not expand beyond the average size of the lumen of the body cavity. Furthermore, as would be understood by those skilled in the art, the expandable member 208 may be modified FIG. 4 is an alternate embodiment of the end-effector 112 wherein the expandable member 208 may include one or more longitudinal struts 402 to provide additional support to its structure. The struts 402 may be arranged in parallel, diagonal, or oblique direction relative to the axis passing between the proximal end 202 and distal end 204 of the expandable member 208. The struts 402 may be connected to the outer or inner surfaces of the arms 206.

The struts 402 may be formed from the same material as the arms 206 of the expandable member 208, for example, shape memory alloys such as nitinol or stainless steel or any other material now known or known in the future suitable for the purpose may be used.

The struts 402 may include suitable coatings, such as antibacterial coatings, lubricious materials, drug-releasing agents, or radiopaque markers. It will be understood that these or any other known medical device coating may be applied to the struts 402 without departing from the scope of the present disclosure.

In each of the embodiments discussed, for ablation purpose a low-pressure fluid that may consist of a wide variety of medicaments. The fluid may include oils, water, homogeneous or heterogeneous solutions, or their combinations.

The fluid may ablate tissue using thermal energy. The fluid may be heated to a suitable temperature range to allow the fluid to ablate a tissue upon contact. Known mechanical or electrical devices may be used for heating the fluid to a desired temperature.

The fluid may operate on a wide pressure range, which may be pre configured or dynamically controlled. The pressure range may be correlated with the pressure of the body cavity requiring tissue manipulation. The pressure range may extend from the pressure of body cavity to the sum of the pressure of the body cavity and the minimum pressure gradient of the body cavity with its adjoining cavities.

The fluid may be stored in the reservoir 116 prior to its application in the device 100, where it resides until it is transported to the body cavity. The reservoir 116 may be a metallic, ceramic, or polymeric container that can contain appropriate amount of fluid required for the ablation procedure. In addition, the reservoir 116 may be connected to the working channels 114 via one or more ports (not shown) on the sheath 102 or the handle 110 of the device 100. Suitable actuators connected to the reservoir 116 may pump the fluid to the working channels 114 and heat the fluid to appropriate temperature required for ablation.

A suitable drainage mechanism may be employed to remove and dispose of the fluid after the procedure. A disposable or re-usable container may be connected to the working channels 114 of the sheath 102 via one or more ports on the sheath 102 or the handle 110. The container may be used as a drainage container to collect the post-procedural fluid. The container may be made up of a metallic, ceramic, polymeric or a composite material. The drainage mechanism may also employ suitable actuators or pumps to pump the extract fluid from the working channels 114 to the drainage container.

In one embodiment of the present disclosure, an intermediate procedure sheath (not shown) with multiple channels may be employed to connect the reservoir, drainage container and other equipment connected to the device 100 to the ports of the sheath 102 or handle 110. The intermediate procedure sheath may be a flexible polymeric or rubber sheath to enable easy operation of the device 100. The intermediate procedure sheath may be insulated with suitable insulation layers to protect the physician and the patient form any inadvertent burns caused by the flow of heated fluid within the channels of the intermediate sheath.

Some embodiments of the present disclosure may also include sensors such as temperature, pressure, impedance or other suitable sensors. These sensors may measure physical quantities required to control the process. The sensors may be employed within the sheath 102, fluid channels or at any other appropriate location to measure suitable physical or chemical characteristics of the fluid and provide feedback signals to the computer.

In addition, the ablation device 100 may include a controller (not shown) coupled to the proximal end 104 of the sheath 102 or to the handle 110. The controller controls a number of operations of the device 100. Controller may manipulate the fluid temperature, pressure, the amount of fluid let into and out of the body cavity, sensors, or other tools employed in the device 100. In addition, the controller may also control the expansion of the expandable member 208, based on body cavity size.

Other variations in the ablation device 100 may be contemplated. For example, the device 100 may include a sealing mechanism that provide an effective seal between the sheath 102 and the body cavity. The sealing mechanism may also be utilized in sealing the end-effector 112 into the body cavity and preventing unwanted leakage during tissue ablation procedure. An effective sealing mechanism may consist of sutures, adhesives, vacuum sealing devices or any other mechanism presently known in the art or may be known in the future. In another embodiment of the present disclosure, end-effector 112 may only contain the basket 208 connected to the distal end 106 of the sheath 102.

Figure 5:
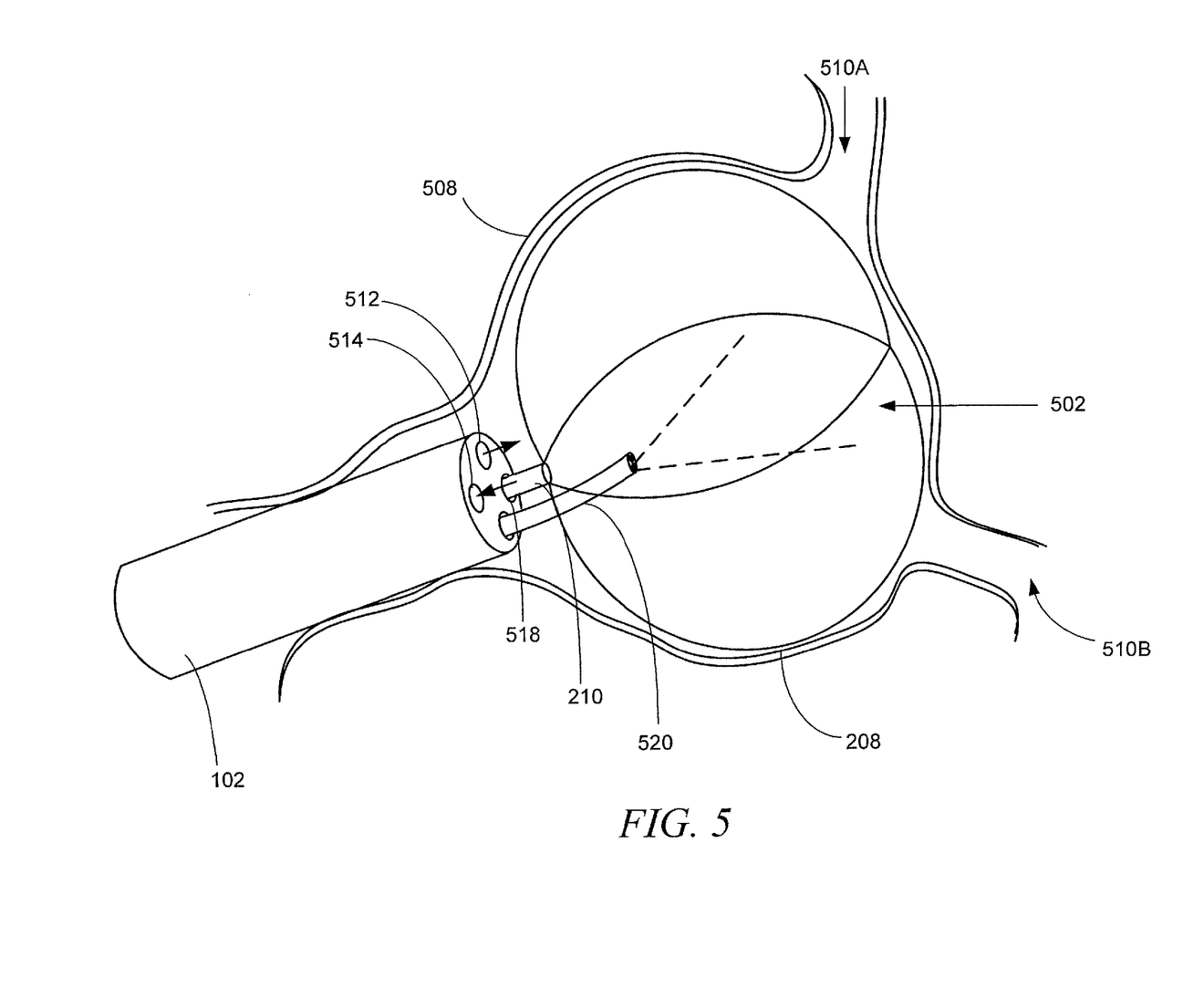
FIG. 5 is an exemplary method of using the medical device, shown in FIG. 1, to ablate a uterine cavity.

FIG. 5 illustrates an exemplary method for ablating a body tissue using the ablation device 100. Specifically, the ablation device 100 ablates endometrial tissue 508 within the uterine cavity 502 of a female reproductive system using a hydrothermal ablation process. It should be understood that the ablation device 100 might be used to ablate other body cavities without departing from the scope of the present disclosure.

The method includes advancing the sheath 102 inside the uterine cavity 502 through the vaginal opening. The proximal end of the sheath 102 having the handle and/or the controller may remain outside the body for control reasons. The sheath 102 may carry the expandable member 208 in a collapsed form. Alternatively, the sheath 102 may be advanced first and the end-effector 112 may be inserted through a channel 518 of the sheath 102. Once sheath 102 is appropriately deployed and sealed inside the uterine cavity, expandable member 208 extends from the distal end 106 of the sheath 102 and expands. This expansion process increases the size of the uterine cavity 502.

Subsequently, the fluid is flushed into the cavity 502 through a working channel 512. The fluid used in this process may be heated saline. In one embodiment, the saline may be heated to a preferable temperature range of 50 to 150 degrees Celsius, and more preferably to a temperature range of 80 to 100 degrees Celsius.

The fluid pressure may be less than the pressure of fallopian tubes 510A and 510B, and may be greater than the uterine cavity pressure. In general, the opening pressure of the fallopian tubes 510A and 510B may be about 70 mmHg, as those skilled in the art will understand. In addition, the pressure of the uterine cavity 502 may vary from about 20 to 40 mmHg. Accordingly, the supplied fluid pressure may be in the range of 10 to 55 mmHg. In one embodiment, the fluid pressure may be about 35 mmHg. As described in greater detail earlier, the exemplary fluid pressure may avoid leakage of fluid into the fallopian tubes 510A, 510B.

The fluid injected through channel 512 remains within the cavity 502 for a desired period of time, which may depend on the extent of ablation required. The physician may choose to set a suitable time period according to the pre-operative conditions of the patient and the physician's experience or a standardized time-period representing average ablation time may apply. The heated saline used, may be flushed into the uterine cavity 502 for a preferable time-period of 5 to 10 minutes, and more preferably for a time-period of 8 to 10 minutes to ablate the tissue. Subsequently, fluid is expelled from the cavity 502 through a fluid outlet channel 514 to the drainage container.

During this process, the physician may choose to introduce other tools through the channel 518 of the sheath 102. For example, a visual device 520, such as a camera, may be introduced to visualize the tissue ablation procedure. It is further noted that any other device may be introduced through the channels of the device 100 without deviating from the scope of the invention, as those skilled in the art will understand.

Once the ablation procedure is complete, the sheath 102 is retracted from the cavity 502. In one embodiment of the present disclosure, the expandable member 208 may be first retracted within the sheath 102 to collapse it, and subsequently, the entire device is retracted.

As discussed, the embodiments of the present disclosure facilitate efficient tissue ablation. To this end, the present disclosure employs a suitable fluid having pressure ranging between the pressure of the uterine cavity 502 and the fallopian tubes 510A and 510B. In addition, the expandable basket 208 operates to increase the uterine cavity size during the ablation process.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A medical device for ablating tissue within a body cavity, comprising:
   a sheath having a lumen extending therethrough from a proximal end to a distal end and first and second channels extending within the lumen;
   an end-effector insertable into the first channel, the end-effector extending from a proximal end to a distal end and including an expandable member having a plurality of arms extending between the proximal end and the distal end, the arms being configured to transition between a collapsed state and an expanded state in which the arms hold a target body cavity in an expanded configuration; and
   a mechanism for transporting a fluid through the second channel to the body cavity to ablate the tissue.

2. The medical device of claim 1, wherein the end-effector further includes an elongate member connected to a proximal end of the expandable member, a proximal end of the elongate member extending out of the proximal end of the sheath.

3. The medical device of claim 1, wherein the expandable member is a basket.

4. The medical device of claim 1, wherein the arms are coupled at a distal end and a proximal end of the expandable member, a middle portion of the arms being configured to expand radially outward in the expanded state.

5. The medical device of claim 1, wherein the fluid is saline.

6. The medical device of claim 1, wherein the fluid is supplied through the second channel at a predetermined pressure.

7. The medical device of claim 6, wherein the predetermined pressure is greater than a pressure of the body cavity and smaller than a pressure of the fallopian tubes.

8. The medical device of claim 1, wherein the sheath further comprises a second channel configured to introduce the fluid into the body cavity and a third channel for removing fluid from the body cavity.

9. The medical device of claim 1, further comprising a strut provided between a pair of the arms.

10. The medical device of claim 1, further comprising a visualization device configured for introduction into the body cavity through a third channel.

11. The medical device of claim 1, wherein body cavity is a uterus.

* * * * *